United States Patent
Leiser et al.

(10) Patent No.: US 7,772,152 B2
(45) Date of Patent: Aug. 10, 2010

(54) COMPOSITE POLYMER-COATED SORBENT WITH A BIDISPERSE PORE SIZE DISTRIBUTION FOR THE SIMULTANEOUS SEPARATION AND DESALTING OF BIOPOLYMERS

(75) Inventors: Robert-Matthias Leiser, Solingen (DE); Dimitri Valerjewich Kapoustine, Moscow (RU); Vitali Pavlovich Zubov, Moscow (RU); Hamlet Balayan, Yerewan (AM); Lutz Plobner, Erkrath (DE); Gottfried Brem, Hilgertshausen (DE)

(73) Assignee: NextTec GmbH, Leverkusen (DE)

( * ) Notice: Subject to any disclaimer, the term of this patent is extended or adjusted under 35 U.S.C. 154(b) by 775 days.

(21) Appl. No.: 10/595,755

(22) PCT Filed: Nov. 10, 2004

(86) PCT No.: PCT/EP2004/012712

§ 371 (c)(1),
(2), (4) Date: Apr. 26, 2007

(87) PCT Pub. No.: WO2005/049198

PCT Pub. Date: Jun. 2, 2005

(65) Prior Publication Data

US 2007/0293394 A1    Dec. 20, 2007

(30) Foreign Application Priority Data

Nov. 10, 2003   (EP) ................................. 03025829

(51) Int. Cl.
*B01J 20/22* (2006.01)
(52) U.S. Cl. .......................... 502/401; 502/439; 502/509
(58) Field of Classification Search ................. 502/401, 502/162, 439, 509, 527.14
See application file for complete search history.

(56) References Cited

U.S. PATENT DOCUMENTS

| 4,160,728 A | 7/1979 | Kirkland et al. |
| 5,522,994 A | 6/1996 | Frechet et al. |

FOREIGN PATENT DOCUMENTS

| EP | 1 020 220 A | 7/2000 |
| WO | WO-00/64579 A | 11/2000 |
| WO | WO-01/96556 A | 12/2001 |

*Primary Examiner*—Edward M Johnson
(74) *Attorney, Agent, or Firm*—Venable LLP; Ann S. Hobbs

(57) ABSTRACT

A composite polymer-coated sorbent with a bidisperse or oligodisperse distribution of pore sizes and having an at least partial coating on its surface, which coating comprises essentially polyanilines or derivatives of polyanilines and use thereof for the simultaneous separation and desalting of biomacromolecules.

14 Claims, No Drawings

COMPOSITE POLYMER-COATED SORBENT WITH A BIDISPERSE PORE SIZE DISTRIBUTION FOR THE SIMULTANEOUS SEPARATION AND DESALTING OF BIOPOLYMERS

The invention is concerned with the use of a composite sorbent comprising a support, which is at least partially covered by a polymeric film based on polyanilin or other primary aromatic amines, as it has been described in WO-A-00/64579. Such sorbents have been successfully used for a very rapid and convenient separation of DNA from other bio-macromolecules. The disadvantage of the technical solution with respect to a extremely accelerated one-step procedure for DNA purification is the rather pure retention of low molecular weight compounds in cell lysates, which usually represent a great amount of inhibitors of DNA modifying enzymes.

WO-A-00/64579 discloses a material which fails to separate low molecular compounds satisfactorily although absorbing proteins and other biopolymers with high capacity except DNA.

As commonly known, a silica gel support by itself can serve as a gel filtration matrix. But the porous structure, which is needed for optimal interaction with proteins and other bio-macromolecules is not suited for a retention of low-molecular weight compounds. Mixing of two silica gel matrices with different pore size characteristics, however, leads to dramatic losses in DNA yield.

The technical problem underlying the present invention is to provide a method and material by which additionally to the separation of biomacromolecules on polyanilin surfaces low molecular weight substances can be efficiently retained on the sorbent.

The technical problem -is solved by a support for the polymeric surface modification, which has a porous structure with a bidisperse or oligodisperse distribution of pore sizes. Such structures build the basis for sorbent materials according to the present invention, which allow additionally to the separation of bio-macromolecules the improved retention of low molecular weight substances.

Surprisingly a bidisperse pore size distribution of the support yields a high DNA amount, accompanied by acceptable protein binding and retention of low-molecular weight compounds.

Preferably the support is an inorganic material selected from the groups comprising inorganic metal oxides preferably with a porous structure such as oxides of aluminium, titanium, zirconium, silicon and/or iron.

In a further embodiment of the invention the support is an organic material preferably with a porous structure such as linear or cross-linked polystyrene, polyethylene, polyacrylate particles or surfaces.

Preferably, the support containing inorganic or organic materials is in particle-like or monolithic membrane-like form and has a porous structure which shows a bidisperse or oligodisperse distribution of pore sizes. Such structures build, e. g., the basis for sorbent materials according to the present invention, which allow additionally to the separation of bio-macromolecules such as nucleic acids or proteins the improved retention of low molecular weight substances having, e. g., molecular weights of less than 500 Da. The skilled person knows how to manufacture bi- or oligodisperse supports to be used according to the Invention. It is also generally known how to adjust ratios of the different disperse phases. For example, such bidisperse supports may preferentially be obtained by means of gelling (gel building) of silica sols, starting the process with the mixture of two size types of monodisperse colloidal silica particles. The mass proportion of these two types of colloidal particles determines the proportion and distribution of differently sized pores in the final silica support material.

Typically, two types of silica sols are prestructured prior to mixing. Prestructuring occurs, e.g., by temperature treatment or other methods and partially evaporating water. The ratio of the mean diameter of the large pore size distribution and the lower pore size distribution is in the range of 3-15, in particular 4-10. The mean diameter of the larger pore size distribution should not be smaller than 25 to 50 nm and should not exceed 2000 nm, in another embodiment 1000 nm.

The composite sorbent with a bidisperse or oligodisperse distribution of pore sizes has preferentially an at least partial coating on the support, which coating comprises essentially polyanilines or derivatives of polyanilines for the separation, isolation, identification, purification (e.g. desalting) and/or detection of biomolecules in particular nucleic acids, proteins, polysaccharides in analytical or preparative scale.

The derivatives of polyaniline are preferably substituted or nonsubstituted alkyl anilines, aromatic systems, ethylaniline, propylanilin, and/or ethoxyanilin.

The following table demonstrates the results of comparable analyses of (a) the primarily sorbent referring to WO-A-64579, (b) a two-layer cartridge with the sorbent referring to WO-A-00/6579 and an additional layer of a gel filtration matrix "BioGel® P10" medium (BioRad), (c) the mixture of two different silica gel matrices with different pore sizes and (d) the bidisperse pore structure sorbent of the invention.

TABLE

Comparison of separation parameters by purifying a DNA lysate from *E. coli* (example 7) using the 4 different sorbent types described above:

| Description of sorbent | Protein retention (% of 500 µg BSA) | Salt retention (% of 1M CuSO4) | DNA recovery (% of applied *E. coli* lysate) |
|---|---|---|---|
| a. sorbent referring to WO-A-00/64579 | 90 | 65 | 70 |
| b. two-layer cartridge | 75 | 98 | 78 |
| c. Sorbent prepared on silica mixed from two fractions differing in the mean pore size diameter (5 nm and 50 nm) | 90 | 65 | 35 |
| d. sorbent referring to the present invention | 95 | 88 | 70 |

The sorbent described in WO-A-00/64579 suffers from bleeding out of loosely bound polymer under the conditions employed, such as sorption, washing etc. The invention overcomes these disadvantages and leads to an economic and competitive process and product (cf. examples 5 and 6).

The main advantages of the use of the composite sorbent as suggested earlier [A. Syed et al. "Polyaniline: Reaction Stoichiometry and Use as an Ionexchange Polymer and Acid/Base Indicator"; *Synthetic Metals,* 36, 209-215(1990); U.S. Pat. No. 5,281,363; 1/1994, Shacklette et al.; 252/500; U.S. Pat. No. 5,232,631; 8/1993, Yong Cao et al.; 252/500; J. Nicolau "Characteristic of Polyaniline filled by Porouse n$^+$-type Silica by the Renthgene Photoelectrical Specthroscopy Method"; *Synthetic Metals,* 1-3, 2073-2074(1995)] are the ease of handling, the speed of the separation process and the possibility of a visual control of sorption and separation processes. DNA is contained in the flow-through (cartridge methods) or in the supernatant (batch methods). Low molecular weight substances are retained in the column and can be washed of separately from the DNA fraction. Bound proteins can be eluted separately by a gradient and subsequently analysed if needed.

The present invention is further illustrated by the following examples, which are understood to be not limiting.

EXAMPLE 1

For the synthesis of sorbents with a bidisperse or oligodisperse distribution of pore sizes, a silica gel has been prepared in the following way:

The two starting types of silica sol in water had following characteristics:

A: particle diameter: 6 nm; $SiO_2$ concentration: 22 mass %; $Na^+$-stabilised pH: 9.1

B: particle diameter: 40 nm; $SiO_2$ concentration: 40 mass %; $Na^+$-stabilised pH: 9.2

Water from the two silica sols was evaporated at pH 5.0 in a water bath at 80° C. by constant stirring until 30 and 60 mass %, respectively. To 100 ml of sol A structured by evaporation were added 50 ml of structured sol B and the evaporation has been continued until the formation of a homogeneous gel. The silica hydrogel obtained after 4 hours sinerethis (partial shrinkage) was dried, first for 4 hours at 80° C. in a water bath, followed by 3 hours at 130° C. in a drying hood. Afterwards the product was treated at 600° C. for 5 hours in a muffel oven. The ready obtained silica gel was grinded, fractionated and analysed for pore size distribution both by mercury porometry (according to DIN 66 133 (1993)) and BET-method (according to ISO 9277). These analyses showed a preferential pore size in two classes of 5 nm and 28 nm, a sorption volume of 0.7 $cm^3$/gr and a specific surface of 120 $m^2$/gr.

EXAMPLE 2

The two starting types of silica sol in water had following characteristics:

A: particle diameter: 10 nm; $SiO_2$ concentration: 30 mass %; $Na^+$-stabilised pH: 9.2

B: particle diameter: 80 nm; $SiO_2$ concentration: 50 mass %; $Na^+$-stabilised pH: 9.1

The silica gel sorbent was prepared as in example 1, with following variations:

Water from the two silica sols was evaporated at pH 4.5 in a water bath at 80° C. by constant stirring until 52 and 60 mass %, respectively. To 100 ml of sol A structured by evaporation were added 130 ml of structured sol B. Analyses showed a preferential pore size in two classes of 7 nm and 60 nm, a sorption volume of 0.75 $cm^3$/gr and a specific surface of 95 $m^2$/gr.

EXAMPLE 3

Synthesis of polyaniline (PANI)-controlled pore glass (CPG) based on unmodified carrier.

Silica (effective pore diameter 50 nm, particle size 100-200 μm, pore surface 75 $m^2$/g) were placed into the glass ampoule and connected with the vacuum source. The ampoule was evacuated to a pressure of about $10^{-3}$ Torr while it was heated in a water bath at 343 K. After closing the vacuum line it was connected to the vessel containing the monomer, dopant and oxidizer. As a result the solution wetted the silica particles and entered the pores. Modification of glass was carried out as follows: 1.5 ml of aniline in 60 ml of 0.8 M HCl and 4.2 g $(NH_4)_2S_2O_8$ in 60 ml of water were mixed and immediately added into the ampoule containing 20 g of CPG. The mixture was incubated under stirring for 30 min at room temperature. The reaction was stopped by addition of 1 M $NH_4OH$ (100 ml) to the suspension. To remove impurities and loosely bound PANI particles of the obtained material were washed on a filter by twenty portions of 100 ml 1 M $NH_4OH$, water to neutralize the pH value of filtrate and then was replaced into 100 ml of water, then by methanol solution (1:1) for 17 h, and then washed with methanol. Finally the sorbent was dried under vacuum.

EXAMPLE 4

Synthesis of PANI-sorbent based on a sulphurated carrier.

Silica (effective pore diameter 50 nm, particle size 100-200 μm) was placed into the glass ampoule and connected to the vacuum source. The ampoule was evacuated to the pressure of about 10-3 Torr while heating to 550K. After that ampoule was cooled to room temperature tetrafluoroethylene was added. The system was kept at room temperature during 6 h, cooled to liquid nitrogen temperature and irradiated by a γ-irradiation source with a dose of 3-10 Mrad and defreezed to room temperature. After polymerization the ampoule was connected to a vacuum source and evacuated to a constant pressure of about $10^{-3}$ Torr. Styrene and divinylbenzene vapors (monomer ratio 9:1) were added and the system was incubated for 4 h. The excess of monomer was removed by heating the ampoule to 350 K. The ampoule was cooled and disconnected from vacuum source. The obtained carrier (20 g) was sulfurated by concentrated sulfuric acid treatment (200 ml) for 90 min at 363 K. The prepared carrier was washed with water to neutralize the pH value of filtrates and dried under vacuum to constant weight. The sulfonate groups surface concentration was defined as 0.109 mmol/g. The polyanilin-coated sorbent was treated as in Example 3. 20 g of the prepared sulfurated carrier was treated by the reaction mixture containing 1.5 ml of aniline in 60 ml of 0.2 M HCl and 4.2 g of $(NH_4)_2S_2O_8$ in 60 ml of water.

To remove impurities and loosely bound PANI particles the obtained material was washed on a filter by five portions of 100 ml 1 M $NH_4OH$, water to neutralize the pH value of the filtrate and then was replaced into 100 ml of water, then by methanol solution (1:1) for 17 h, and then washed with methanol.

EXAMPLE 5

Synthesis of Poly-o-Toluidine (PT)-sorbent

PT was synthesized by chemical oxidizing polymerization of o-toluidine. 2.6 ml of o-toluidine was dissolved in 100 ml of 1M HCl. The solution was kept at 0-5° C. in an ice bath. Aqueous solution of 0.1M ammonia persulfate (5.7 g) was added dropwise during 0.5 h under stirring. The final volume of the reaction mixture was 250 ml. The reaction mixture was stirred for 1 h and kept for 24 h at 10° C. The obtained sediment was filtered, washed with water, methanol and acetone. 1 g of the polymer salt was suspended in 250 ml of 0.05 M of $NH_4OH$ solution and stirred for 12 hours. The it was filtered and washed with 250 ml of 0.05 M $NH_4OH$ solution and water to neutralize the pH value of the filtrates. The product was dried to constant weight under vacuum. Poly-o-toluidine (1.6-0.9 g) was dissolved in 100 ml of tetrahydrofurane (THF). 10 g of silica (effective pore diameter 50 nm, particle size 100-200 μm) was placed into a glass ampoule and connected to a vacuum source. The ampoule was evacuated to a residual pressure of about $10^{-3}$ Torr during heating in a water bath at 343 K. Then the vacuum line was closed and the ampoule connected to a vessel containing the polymer solution. Hereby the solution wetted the silica particles and entered the pores. The reaction mixture was sonificated for 15 min. The solvent was removed from the ampoule under vacuum. The pepared sorbent was washed with 1-3 portions (100 ml) of water, replaced into 50 ml of water-methanol solution (1:1) for 17 h and then washed by methanol, acetone, water and dried under vacuum to constant weight. No loosely bound PANI particles were observed in the filtrates.

EXAMPLE 6

Synthesis of PANICT-sorbent

Poly-[aniline]-co-[o-toluidine] (monomer ratio 1:4) (PANICT) was synthesized by chemical oxidizing polymerization as in Example 5. 2.08 ml of o-toluidine and 0.44 ml of aniline were dissolved in 100 ml of 1M HCl. 10 g of Silica (effective pore diameter 50 nm, particle size 100-200 μm) was coated with the obtained copolymer solution in THF as in Example 5 (1.6 g of cotelomer was dissolved in 100 ml of THF). The prepared sorbent was washed with methanol, acetone, water and dried under vacuum to constant weight. No loosely bound PANI particles were observed in the filtrates.

EXAMPLE 7

The described modified sorbents were used for the purification of genomic DNA from lysates of *Escherichia coli*.

1. An overnight culture was made from the strain *E. coil* JM 109 (50 μl bacteria cells, 10 ml medium, 37° C.).
2. From this culture 1 ml was centrifugated in micro centrifuge tubes.
3. After removal of the supernatant the bacterial pellet was suspended in 100 μl buffer 1 (2 mg/ml lysozyme, 2 mM $CaCl_2$, 100 mM Tris-HCl pH 7.9, 4% succrose).
4. For cell lysis the suspension was incubated for 8 min at 60° C.
5. 100 μl buffer 2 were added (1% MIRA Tensid-Mix, 1.5 mM EDTA) and cooled to room temperature.
6. The mixture was shaken 10 min at room temperature and incubated for further 5 min without shaking at room temperature.
7. The mixture was centrifuged for 2 min at 13,000 rpm.
8. The supernatant was given onto a sorbent-packed column and eluted with TE-buffer.

Preparation and Use of the Sorbent

The sorbent is subsequently wetted in methanol, 50% methanol and water and then degassed for 0.5 h. The supernatant is decanted and the sorbent washed 4 times with TE buffer. While stirring the sorbent in TE buffer it is degassed under vacuo in an exciccator. Cartridges are packed with this suspension of the sorbent (120 mg/ml).

A bacterial lysate (see above, step 8) from 1 ml of overnight culture is prepared and pipetted onto the cartridge and eluted with TE buffer. The cartridge is incubated 5-10 min without elution. Five fractions with volume of 200 μl are collected immediately after the cartridge starts to drop. The fractions are further analysed by agarose gel electrophoresis (0.8% agarose in 89 mM Tris; 89 mM boric acid; 2 mM EDTA) at a constant current of 100 mA.

Gels are stained with ethidium bromide. Genomic DNA but not RNA is found in the second fraction. The DNA containing fraction is measured in a spectrophotometer. The ratio of the absorption $A_{260}$:$A_{280}$ of such fractions is in the range of 1.58 to 1.78.

The invention claimed is:

1. A composite polymer-coated sorbent comprising a support and a coating, wherein the support comprises a bidisperse or oligodisperse distribution of pore sizes and at least a partial coating on the surface or the sorbent, which coating comprises essentially polyanilines or derivatives of polyanilines.

2. The sorbent according to claim 1 wherein the support is a porous inorganic material selected from the group comprising inorganic metal oxides.

3. The sorbent according to claim 1 wherein the support is an organic material.

4. The sorbent according to claim 2, wherein the inorganic material has a bidisperse distribution of the pore sizes and is obtainable by gelling a mixture of two silica sols with differently sized colloidal silica particles.

5. The sorbent according to claim 1 wherein the support is in particle-like or monolithic membrane-like form.

6. The sorbent according to claim 1, wherein the derivatives of polyaniline are substituted or nonsubstituted alkyl anilines, aromatic systems, ethylaniline, propylanilin, and/or ethoxyanilin.

7. The sorbent according to claim 1 wherein the support comprises a bidisperse distribution of small pore sizes in the range of mean diameter 3-15 nm.

8. The sorbent according to claim 1 wherein the support comprises a bidisperse distribution of large pore sizes in the range of mean diameter not smaller than 25-50 nm but not exceeding 2000 nm.

9. A method for the simultaneous separation and purification of bio-macromolecules comprising using the composite of claim 1.

10. The sorbent of claim 2, wherein the inorganic metal oxides are oxides of aluminium, titanium, zirconium, silicon oxides, and/or iron oxides.

11. The sorbent according to claim 3, wherein the support material has a porous structure.

12. The sorbent according to claim 3, wherein the support material is cross-linked polystyrenes, polyacrylates, and polyethylenes.

13. The support of claim 7, wherein the mean diameter is in the range of 4-10 Nm.

14. The support of claim 8, wherein the mean diameter does not exceed 1000 nm.

* * * * *